United States Patent [19]
Chiou

[11] Patent Number: 5,344,829
[45] Date of Patent: Sep. 6, 1994

[54] USE OF OB-101 TO TREAT INFLAMMATION

[75] Inventor: George C. Y. Chiou, College Station, Tex.

[73] Assignee: The Texas A&M University System, College Station, Tex.

[21] Appl. No.: 103,255

[22] Filed: Aug. 6, 1993

Related U.S. Application Data

[63] Continuation-in-part of Ser. No. 801,891, Dec. 3, 1991, Pat. No. 5,194,434.

[51] Int. Cl.$^5$ ............................................. A61K 31/535
[52] U.S. Cl. ................... 514/227.2; 514/912; 424/427; 424/429
[58] Field of Search .................... 514/227.2, 912; 424/427, 429

[56] References Cited

U.S. PATENT DOCUMENTS

| | | | |
|---|---|---|---|
| 3,896,223 | 7/1975 | Ariyan et al. | 424/248 |
| 4,450,159 | 5/1984 | Anderson et al. | 424/246 |

FOREIGN PATENT DOCUMENTS 57-171986  10/1982  Japan .

OTHER PUBLICATIONS

Hoover, J. E., et al., eds., *Remington's Pharmaceutical Sciences* (1975) 15th Edition, pp. 1491–1492.

Polansky, J. R., et al., "Anti–inflammatory agents: steroids as anti–inflammatory agents" Sears, ed., *Handbook of Experimental Pharmacology* Springer–Verlag, (1985) 69:459–538.

Miyano, K., et al., "Pharmacological prevention of ocular inflammation induced by lens proteins" *Ophthalmic Res.* (1984) 16:256–263.

Chiou, L. Y., et al., "Ocular anti–inflammatory action of a lipooxygenase inhibitor in the rabbit" *J. Ocular Pharmacology* (1985) 1(4):383–390.

Bhattacherjee, P., et al., "Effect of lipooxygenase products on leukocyte accumulation in the rabbit eye" *Leukotrienes and Other Lipooxygenase Products,* Samuelsson, B., et al., eds., Raven Press, New York, (1988) pp. 325–330.

Chang, M. S., et al., "Prevention of lens protein-induced ocular inflammation with cycloxygenase and cycloxygenase and lipooxygenase inhibitors" *J. Ocular Pharmacology* (1989) 5(4): 353–360.

Walsh, J. B., et al., eds., *Physicians' Desk Reference for Ophthalmology,* Edward R. Barnhart, Publisher, 16th edition, (1988) p. 9.

*Primary Examiner*—Zohreh Fay
*Attorney, Agent, or Firm*—Morrison & Foerster

[57] ABSTRACT

A novel compound for the treatment and prevention of ocular and other types of inflammation is disclosed. The compound, OB-101, is effective at both the early and late phases of inflammation. The compound is useful for the treatment of inflammation in both the anterior and posterior portions of the eye, as well as in other parts of the body.

5 Claims, 7 Drawing Sheets ns to PCT application
USE OF OB-101 TO TREAT INFLAMMATION

CROSS-REFERENCE TO RELATED APPLICATIONS

This is a continuation-in-part of U.S. Ser. No. 07/801,891, filed Dec. 3, 1991, now issued as U.S. Pat. No. 5,194,434, and corresponds to PCT application PCT/US92/10424 filed Dec. 3, 1992, now pending.

TECHNICAL FIELD

The present invention relates generally to the treatment and prevention of inflammation, particularly ocular inflammation. More specifically, it relates to a novel compound to treat inflammation which has been shown to be an effective ocular antiinflammatory agent.

BACKGROUND ART

Inflammation is a response to tissue injury and comprises complex reactions involving vascular and connective tissues. It can involve any part of the body, such as the joints (arthritis), bowel (inflammatory bowel disease), and lungs (pulmonary inflammation). Inflammation can be mild and self-limited or prolonged and seriously debilitating. Numerous drugs have been developed to fight inflammation. The most prominent in current treatment are anti-inflammatory steroidal drugs, such as prednisolone, and non-steroidal antiinflammatory agents (NSAIAs), such as indomethacin. To predict the effects of drugs on systemic inflammation, investigators have long used inflammatory conditions of the eye because inflammation is easy to observe in the eye.

Ocular inflammation may occur in many different areas of the eye. One type of ocular inflammation, uveitis, is the inflammation of the uveal tract. Endogenous uveitis is caused by various systemic processes or intraocular disorders whereas exogenous uveitis is the result of the accidental introduction of pathogenic organisms or foreign substances into the eye. Endogenous uveitis may be classified in many ways, including anterior, posterior and diffuse. The most commonly occurring types of uveitis, such as histoplasmosis, toxoplasmosis and toxocariasis, affect the posterior part of the eyes which are difficult, if not impossible, for locally instilled eye drugs to reach. Peripheral uveitis, ankylosing spondylitis, herpes simplex, herpes zoster, tuberculosis and endophthalmitis phacoanaphylactica occur in the anterior part of the eyes. Toxoplasmosis, peripheral uveitis, syphilis, tuberculosis, sarcoidosis and Vogt-Koyanagi-Harada syndrome may occur in both the anterior and posterior segments of the eye. Although the etiology of these diseases can be different, they have the common manifestation of ocular inflammation.

Uveitis has been treated with corticosteroids, non-steroidal anti-inflammatory agents, immunosuppressives and a combination of cycloplegics and mydriatics. However, treatment of uveitis with drugs used to treat systemic disorders is not always effective. (Ellis, *Ocular Therapeutics and Pharmacoloy*, C. B. Mosby Co., (1985) pp. 212–227.) Furthermore, very high doses of corticosteroids (100 mg daily) must be used in severe and acute posterior uveitis. Such doses can cause severe complications. Thus, the amounts administered should be reduced when clinical improvement occurs. However, reduction below 15–20 mg/day can result in reoccurrences of the disease.

Since uveitis is considered to be an autoimmune disease, treatment with immunosuppressive agents, such as alkylating agents and antimetabolites, including the drug cyclosporine, is being studied. However, the use of these agents may produce many serious side effects, including bone marrow depression, thrombocytopenia, leukopenia, bleeding, nausea, vomiting and stomatitis. The use of these substances in the treatment of uveitis is still investigational.

In order to avoid serious side effects in the treatment of uveitis, non-steroidal anti-inflammatory agents (NSAIAs) such as salicylates, phenylbutazone, indomethacin, ibuprofen and naproxen have been tried. The results have not been satisfactory. Furthermore, these NSAIAs also can produce numerous side effects, including edema, nausea, stomatitis, epigastric pain, peptic ulcer, agranulocytosis, hepatitis and drug rash.

Ocular inflammation may additionally occur in the anterior portion of the eye following ocular surgery. Steroidal and nonsteroidal antiinflammatory agents have been used to relieve the inflammation. However, steroidal agents can induce an increase in intraocular pressure (Polansky et al., "Antiinflammatory Agents" in , Sears, ed., *Handbook of Experimental Pharmacology*, Springer-Verlag, (1985), 69:459–538). NSAIAs may actually worsen the inflammation, especially during the late phase of the inflammation. This is because the clinically available NSAIAs at this time are primary cyclooxygenase inhibitors. Blocking the cycloxygenase arm of the arachidonic acid (AA) cascade potentiates the production of lipooxygenase metabolites which are ultimately the leukotrienes (LT). LTs are responsible for the late phase of inflammation and for the chemotaxis of leukocytes (Miyano et al., *Ophthalmic Res.* (1984) 16.:256–263; Chiou et al., *J. Ocular Pharmacology* (1985) 1:383–389; Bhattercherjee et al., "Effects of lipooxygenase products on leukocyte accumulation in the rabbit eye" in Samuelsson et al., eds., *Leukotrienes and Other Lipooxygenase Products*, Raven Press (1982) 325–330.) A previous study indicated that a new synthetic lipooxygenase inhibitor, REV 5901, was effective in reducing the late phase of inflammation. However, when REV 5901 was used alone in treatment of lens protein induced ocular inflammation, there was an increase in the early phase of inflammation. This observation was attributed to an increase in the production of prostaglandins caused by the inhibition of the lipooxygenase arm of the AA cascade. (Chang et al., *J. Ocular Pharmacology*, (1989) 5:353–360). The early phase of the inflammation has been effectively suppressed by indomethacin.

DISCLOSURE OF THE INVENTION

The present invention relates to a method for the prevention and treatment of ocular inflammation. In one embodiment, the invention is drawn to the use of a new agent, OB-101, as an ocular antiinflammatory agent. The formula of this compound is as follows:

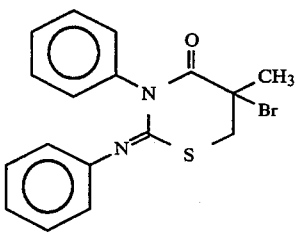

In a second embodiment, the invention involves a pharmaceutical preparation for use in the prevention and treatment of ocular inflammation which comprises the above compound in admixture with a pharmaceutically acceptable excipient.

In a third embodiment, the invention provides a method for treating and preventing inflammation in an animal subject. The method comprises administering an inflammation-controlling effective amount of a pharmaceutical composition of a vehicle and the following compound:

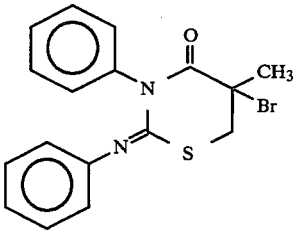

MODES FOR CARRYING OUT THE INVENTION

Figure 1:
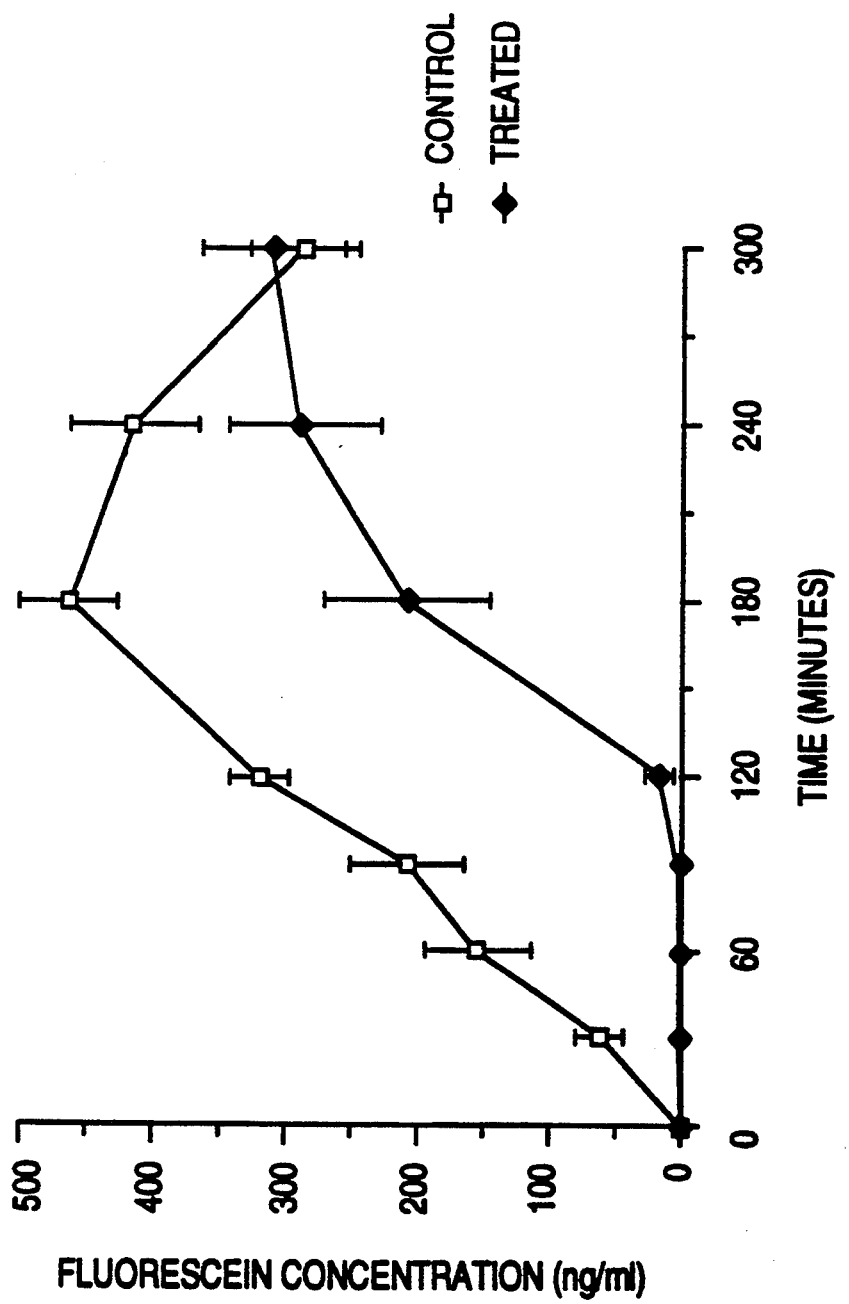
FIG. 1 shows a comparison of the effects of 1% indomethacin on ocular inflammation induced by lens protein injected intracamerally to that of a control that received no drug. Each point is a mean of 9 values for fluorescein concentration in the anterior chamber of the eye. The bars represent the standard error of the mean ("SEM").

The present invention is applicable to ocular inflammation at both the early and late phases of inflammation. OB-101 has been tested for suppression of ocular inflammation and found to reduce inflammation induced in the iris, the ciliary body and the retina. Further tests indicate that OB-101 is also useful for the treatment of posterior uveitis. Additionally, unlike the non-steroidal antiinflammatory agents (NSAIAs), OB-101 does not significantly affect the arachidonic acid cascade metabolism and it does not produce the numerous side effects associated with corticosteroids. These results further indicate the usefulness of OB-101 in other types of inflammation.

OB-101 can be used in many other inflammatory conditions. OB-101 can be used in other ophthalmic disorders including, but not limited to, iritis, iridocyclitis, chorioretinitis, uveitis optic neuritis, sympathetic ophthalmia, herpes zoster ophthalmicus, anterior segment inflammation, allergic conjunctivitis, keratitis, allergic corneal marginal ulcers. OB-101 can be used in rheumatic disorders including, but not limited to, post-traumatic osteoarthritis, synovitis of osteoarthritis, rheumatoid arthritis, bursitis, epicondylitis, tenosynovitis, gouty arthritis, psoriatic arthritis, and ankylosing spondylitis. OB-101 also can be used in allergic states including, but not limited to, bronchial asthma, contact dermatitis, seasonal or perennial allergic rhinitis, drug hypersensitivity reactions, urticarial transfusion reactions and acute noninfectious laryngeal edema. Gastrointestinal inflammation in which OB-101 can be used include, but are not limited to, ulcerative colitis and regional enteritis. Respiratory disorders in which OB-101 can be used include, but are not limited to, symptomatic sarcoidosis, berylliosis, pulmonary tuberculosis (with concomitant antitubercular chemotherapy), aspiration pneumonitis, and Loeffler's syndrome.

DEFINITIONS

In this specification and in the claims which follow, reference will be made to a number of terms which shall be defined to have the following meanings:

"Treatment" as used herein refers to the reduction or elimination of inflammation (therapy).

"Prevention" refers to the treatment of surgical patients to avoid inflammation (prophylaxis).

"Inflammation-controlling effective amount" refers to the amount of the pharmaceutically active substance sufficient to elicit at least a desired threshold response to the substance in a subject to which the substance is administered, whether therapeutic or prophylactic.

"Pharmaceutically active substance" as used herein refers to a substance that has been shown to be useful in the treatment of ocular inflammation. In the present invention, pharmaceutically active substances include OB-101, indomethacin, REV 5901, and prednisolone.

"Pharmaceutical composition" refers to a composition containing the pharmaceutically active substance. The composition may also contain a pharmaceutically acceptable vehicle.

PROCESS FOR PREPARATION

OB-101 may be prepared according to the methods described in Okawara et al. *Chem. Pharm. Bull* 31(2) 507–512 (1983). The synthesis scheme is described in Example 1 below.

ADMINISTRATION

The administration of OB-101 described herein can be via any of the accepted modes of administration of pharmaceutical compositions. These methods include topical administration of solutions, suspension ointments or gels, parenteral injection, or oral administration.

Depending on the intended mode of administration, the compositions may be in the form of solid, semi-solid or liquid dosage forms, such as for example, tablets, pills, capsules, powders, liquids, suspensions, or the like, preferably in unit dosage forms suitable for single administration of precise dosages. The compositions will include a conventional pharmaceutical vehicle and, in addition, may include other medicinal agents, pharmaceutical agents, carriers, adjuvants, diluents, etc. The amount of active compound administered will, of course be dependent on the subject being treated, the manner of administration and the judgment of the prescribing physician.

The conventional pharmaceutical vehicle should be compatible with the pharmaceutically active substance of the pharmaceutical composition. Suitable vehicles for ocular use are, for example, sterile isotonic solutions such as isotonic sodium chloride or boric acid solutions. These vehicles typically contain sodium chloride or boric acid, respectively, as well as benzalkonium chloride and sterile distilled or purified water. Also useful is phosphate buffered saline (PBS), pH 7.4. Other suitable vehicular constituents include phenylmercuric nitrate, sodium sulfate, sodium sulfite, disodium phosphate and monosodium phosphate.

The compositions may also contain auxiliary substances i.e. antimicrobial agents such as chlorobutanol, parabens or organic mercurial compounds; pH adjusting agents such as sodium hydroxide, hydrochloric acid or sulfuric acid; and viscosity increasing agents such as methylcellulose. One of ordinary skill in the art will easily find substitutions for the above auxiliary substances. The final composition should be sterile, essentially free of foreign particles, and have a pH that allows for optimum drug stability. Generally pH values in the range of 5–8 will find use with the subject composition. Preferably, the pH will be as close to the pH of tear fluid, i.e. 7.4, as possible for topical administration to the eye.

Typically the compositions of the subject invention are prepared as solids, solutions, suspensions, ointments, gels, or ocular delivery devices such as drugimpregnated solid carriers that are inserted into the eye. If such a carrier is used, the above-mentioned vehicles are unnecessary. A variety of polymers can be used to formulate ophthalmic drug carriers. Saettone, M. F., et al., *J. Pharm. Pharmacol.* (1984) 36:229, and Park, K. et al., in *Recent Advances in Drug Delivery Systems,* Anderson et al., eds., Plenum Press (1984), 163–183, describe such polymers, the disclosures of which are incorporated herein by reference in their entirety. Drug release is generally effected via dissolution or bioerosion of the polymer, osmosis, or combinations thereof. The device should be formulated to release the drug at a rate that does not significantly disrupt the tonicity of tear fluid.

More specifically, several matrix-type delivery systems can be used with the subject invention. These systems are described in detail in Ueno et al., "Ocular Pharmacology of Drug Release Devices" in Controlled Drug Delivery, Bruck, ed., vol. II, Chap 4, CRC Press Inc. (1983), the disclosure of which is incorporated herein by reference in its entirety. Such systems include hydrophilic soft contact lenses impregnated or soaked with the desired drug, as well as biodegradable or soluble devices that need not be removed after placement in the eye. These soluble ocular inserts can be composed of any degradable substance that can be tolerated by the eye and that is compatible with the drug to be administered. Such substances include but are not limited to poly(vinyl alcohol), polymers and copolymers of polyacrylamide, ethylacrylate, and vinylpyrrolidone, as well as cross-linked polypeptides or polysaccharides, such as chitin.

Capsule-type delivery systems will also find use for oral or ocular delivery of the instant invention. These systems, described in Ueno et al., supra, utilize polymer membranes to control the release of the drug in question. These devices are particularly useful for the delivery of hydrophilic drugs. Hydrophobic drugs can be administered via a silicone rubber device such as described in Ueno et al., supra.

Ophthalmic ointments will include a base, generally composed of white petrolatum and mineral oil, often with anhydrous lanolin. Polyethylene-mineral oil gel is also satisfactory, as are other substances that are nonirritating to the eye, permit diffusion of the drug into the ocular fluid, and retain activity of the medicament for a reasonable period of time under storage conditions. If suspensions are used, the particle sizes therein should be less that 10 $\mu$m to minimize eye irritation. Furthermore, if solutions or suspensions are used, the amount delivered to the patient should not exceed 50 $\mu$l preferably 25 $\mu$l or less, to avoid excessive spillage from the eye.

For solid compositions, conventional nontoxic solids including, for example, pharmaceutical grades of mannitol, lactose, starch, magnesium stearate, sodium saccharin, talc, cellulose, glucose, sucrose, magnesium carbonate, and the like may be used. Liquid pharmaceutically administrable compositions can, for example be prepared by dissolving, dispersing, etc. an active compound as defined above and optional pharmaceutical adjuvants in a vehicle, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975.

For oral administration, i.e., of any of the present compounds which may be orally active, a pharmaceutically acceptable nontoxic composition is formed by the incorporation of any of the normally employed vehicles described above. Such compositions take the form of solutions, suspensions, tablets, pills, capsules, powders, sustained-release formulations and the like. Such compositions may contain 1%-95% active ingredient, preferably 1-10%. An inflammation-controlling effective amount for purposes of preventing or treating inflammation, including ocular inflammation, is usually in the range of 1-50 mg/kg. In order to prevent inflammation in surgical patients, the compound should be administered prior to surgery. For example, the compound may be administered 2-15 hours prior to surgery. Preferably, the compound is administered in multiple doses every 2-6 hours for 10-15 hours prior to surgery. For best results, the compound is administered 12, 8, and 2 hours prior to surgery. Similarly, the compound should, for best results, be administered following surgery in multiple doses. For example, the compound can be administered for 3-10 days post surgery every 4-8 hours. Preferably, the compound is administered every 6 hours following surgery for 5-7 days. In order to treat inflammation, the compound should be administered every 4-8 hours for 3-10 days. Preferably, the compound is administered every 6 hours for 5-7 days.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable vehicles are, for example, water, saline, dextrose, glycerol, ethanol or the like. In addition, if desired, the pharmaceutical compositions to be administered may also contain minor amounts of nontoxic auxiliary substances such as wetting or emulsifying agents, pH buffering agents and the like, such as, for example, sodium acetate, sorbitan monolaurate, triethanolamine oleate, etc. An inflammation-controlling effective amount for purposes of preventing or treating ocular inflammation is usually in the range of 0.1-20 mg/kg. The compound is administered as described above with regard to oral administration.

The subject compounds can also be administered by implantation of a slow-release or sustained-release system, such that a constant level of dosage is maintained. For a review of these sustained release systems see Ueno, et al., "Ocular Pharmacology of Drug Release Devices" in *Controlled Drug Delivery*, Bruck, ed., vol. II, Chap 4, CRC Press Inc. (1983). An inflammation-controlling effective amount for purposes of preventing or treating inflammation, including ocular inflammation, is usually in the range of 0.1-20 mg/kg/day. The system can be implanted after surgery in order to prevent inflammation. In order to treat inflammation, a new implant is inserted every 3-10 days for up to 60 days. Preferably, a new implant is inserted every 5-7 days for up to 30 days.

Topical administration of OB-101 in the form of eyedrops was found to be effective in inhibiting anterior ocular inflammation induced by lens protein injected into the anterior chamber. These results indicate that OB-101 can cross the cornea barrier effectively to inhibit the inflammation inside the eyeball. It is therefore reasonable to assume that OB-101 also can cross the blood eye barrier and inhibit uveitis after systemic administration. The results obtained in this study supported the prediction well. An inflammationcontrolling effective amount for purposes of preventing or treating ocular inflammation is usually in the range of 0.1-20 mg/kg. The compound is administered as described above with respect to oral administration.

Eyedrops are most effective for inflammation of the anterior portion of the eye. For posterior uveitis, injection or oral administration is preferred.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLES

Example 1

Synthesis of OB-101

This example describes the preparation of 5-bromotetrahydro-5-methyl-3-phenyl-2-phenylimino-4-H-1,3-thiazin-4-one (OB-101) according to Scheme 1.

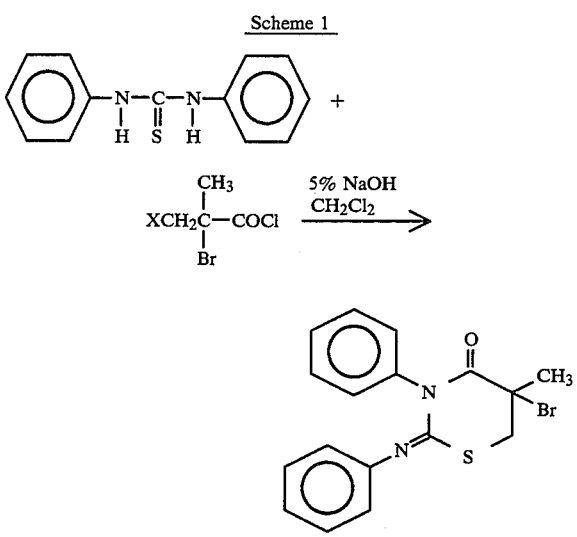

OB-101 can be synthesized as described in Okawara et al. *Chem. Pharm. Bull* 31(2) 507-512 (1983). Briefly, bromoacylchloride (5 mmol) is added dropwise to a stirred solution of 1,3-diphenyl thiourea (5 mmol) in a solution of 5% sodium hydroxide (5 ml) and dichloromethane (30 ml). The solution is constantly cooled with ice-water and kept alkaline by adding 5% NaOH. When the addition is over, 5 ml of 5% NaOH is further added to the reaction mixture, and stirring is continued for 12 hours at room temperature. The $CH_2Cl_2$ layer is separated, washed with $H_2O$ (15 ml× 2), dried over anhydrous $Na_2SO_4$ and evaporated to dryness. The residue is purified by recrystallization from EtOH or by silica-gel column chromatography (benzene:AcOEt=2:1) to yield 5-bromotetrahydro-5-methyl-3-phenyl-2-phenylimino-4-H-1,3-thiazin-4-one (OB-101).

Example 2

Effects of Various Compositions on Lens Protein Induced Inflammation

A. Materials

Indomethacin was purchased from Sigma (St. Louis, Mo.). REV 5901 was obtained from Revlon Health Care Group (Tuckahoe, N.Y.). A 1% ophthalmic solution of prednisolone (1% Econopred) was purchased from Alcon (Fort Worth, Tex.). OB-101 was obtained from Drs. M. Furukawa and T. Okawara at the University of Kumamoto. Indomethacin, REV 5901 and OB-101 were dissolved in polyethylene glycol (molecular weight 200) (60%) and then diluted with aqueous solution (40%) to a final concentration of 1%.

Fluorescein labeled dextran with molecular weight of 70,000 (FD 70) was obtained from Sigma. 100 mg of FD 70 was initially dissolved in phosphate buffer saline (Sigma) and passed through a PD 10 column (Pharmacia). This solution was then diluted with heparinized normal saline to make a final concentration of a vehicle of 10 mg/ml FD 70 and 100 U/ml of heparin.

Lens protein was prepared and protein concentration was determined according to procedures described in Miyano et al. *Ophthalmic Res.* (1984) 16:256-263. The quantity of lens protein in the lens protein preparation was 29.67 mg/ml.

B. Methods

New Zealand White albino rabbits of either sex weighing 2.0 to 3.0 kg were used. The rabbits were initially anesthetized with 25 mg/kg of ketamine and 5 mg/kg of xylazine given intramuscularly. Half of the above dosage was given hourly for the remainder of the experiment. 15 minutes after the anesthesia, 50 μl of the solvent was instilled into the right eye. 50 μl of drug solution was instilled into the left eye. One hour after the application of the drug and the vehicle, 24 μl of the lens protein was injected into the anterior chamber with a 30 gauge needle. Extreme care was taken to avoid traumatizing the iris. Fifteen minutes after the injection of the lens protein, FD 70 (1.4 mg/kg) was injected via a marginal ear vein. The rabbits were euthanized at the end of the experiment with an injection of 10 ml of air through the marginal ear vein.

Scanning of the eyes was done by the use of a fluorophotometer (Fluorotron Master, Coherent Corp., Palo Alto, Calif.). Measurements were done at 0, 30, 60, 90, 120, 180, 240, and 300 minute intervals. The measurements are reported in FIGS. 1-4 and are expressed in ng/ml of FD 70 in the anterior chamber.

C. Results

All data were analyzed with Student's t-test for two values and analysis of variance for more than two values. Each value was expressed as mean ± standard error of the mean. A p value of 0.05 or less was considered significant.

FIGS. 1-4 describe the effects of the various compounds on lens protein induced inflammation. The greater the permeability of fluorescein from the blood stream into the eye, the greater the degree of inflammation.

Figure 2:
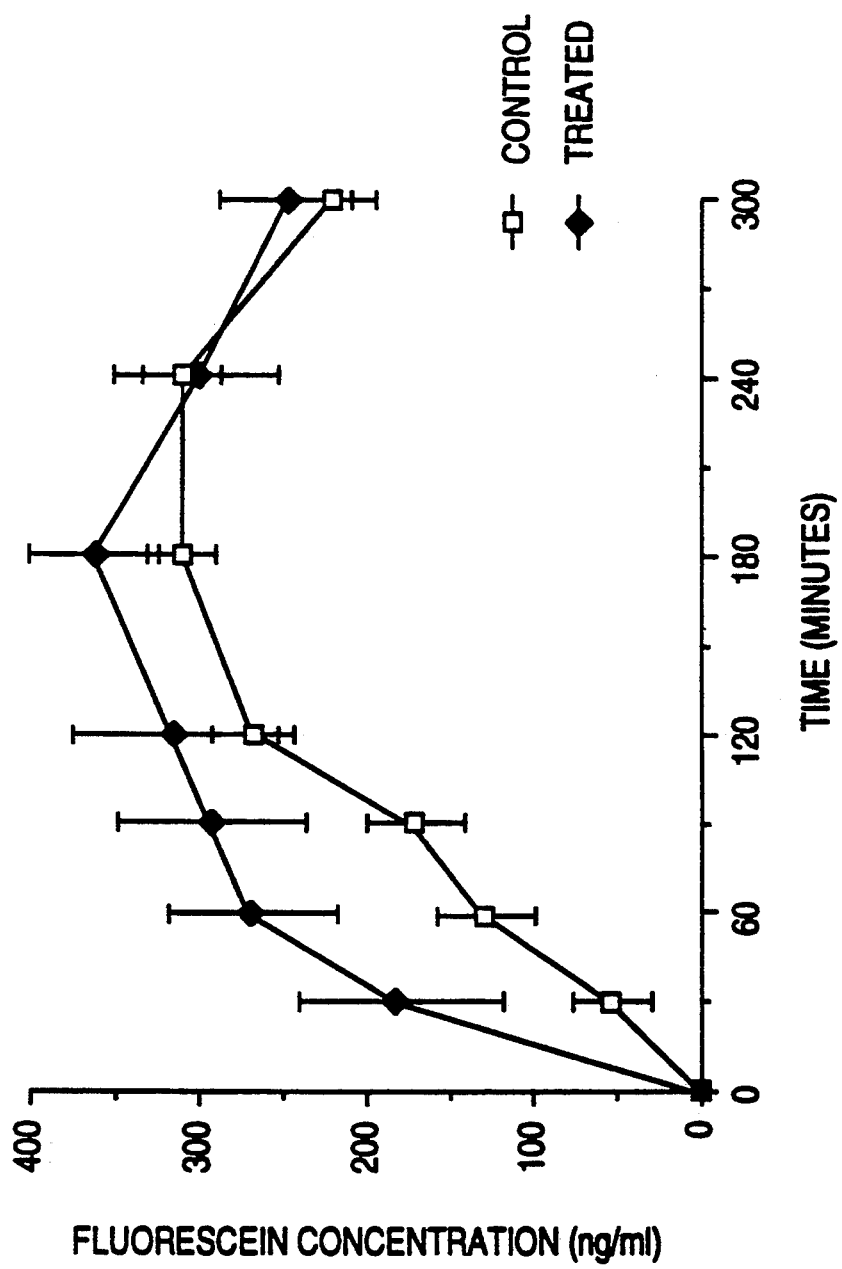
FIG. 2 depicts the effects of 1% REV 5901 on ocular inflammation induced by lens protein injected intracamerally as opposed to that of a control without the drug. Each point is a mean of 9 values for fluorescein concentration in the anterior chamber of the eye. The bars represent the SEM.
Figure 3:
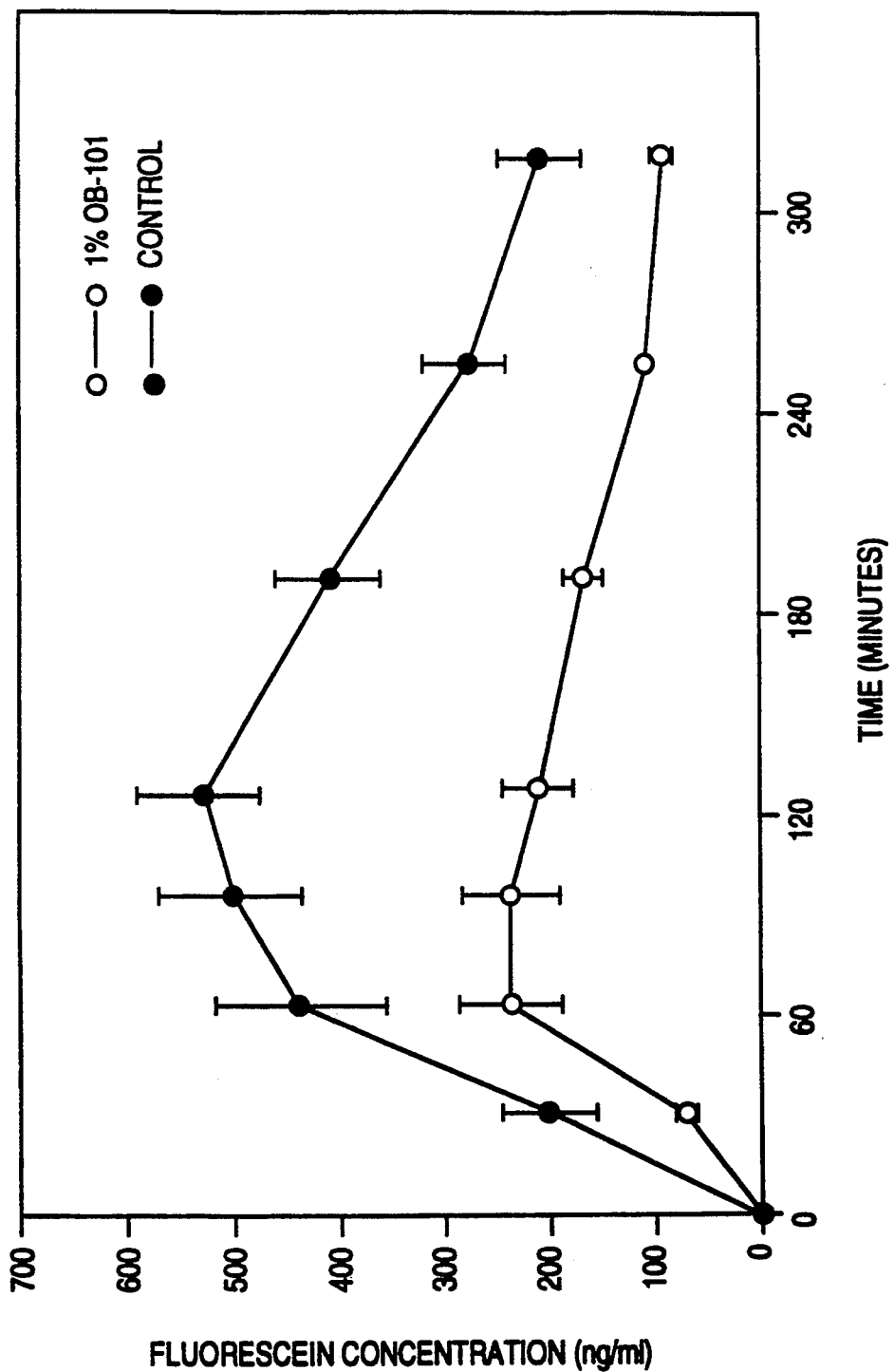
FIG. 3 shows a comparison of the effects of 1% OB-101 on ocular inflammation induced by lens protein injected intracamerally to that of a control that received no drug. Each point is a mean of 6 values for fluorescein concentration in the anterior chamber of the eye. The bars represent the SEM, and the asterisks indicate the significant difference from the corresponding control values at $p<0.05$.
Figure 4:
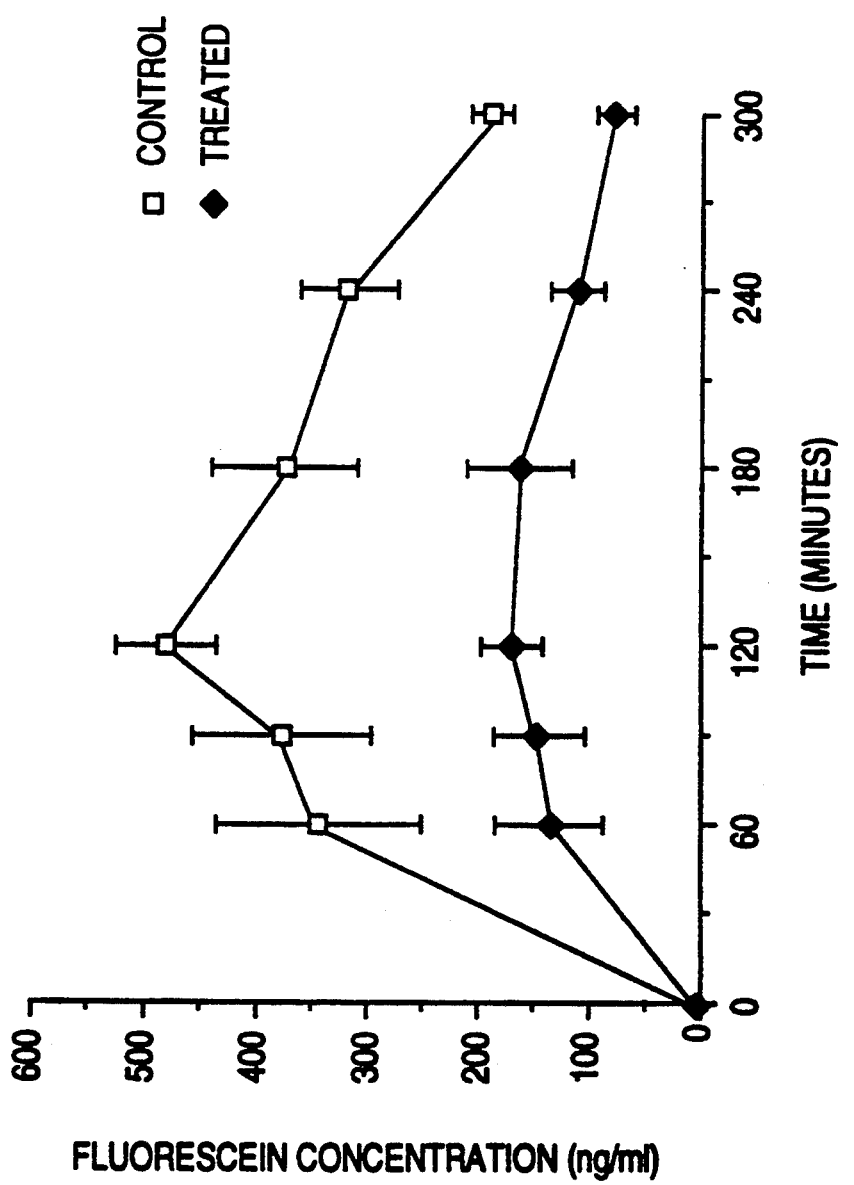
FIG. 4 depicts the effects of 1% prednisolone on ocular inflammation induced by lens protein injected intracamerally as opposed to that of a control without the drug. Each point is a mean of 5 values for fluorescein concentration in the anterior chamber of the eye. The bars represent the SEM.

The early phase of this lens protein induced inflammation (0-3 hours) was effectively suppressed by indomethacin but not the late phase (4-5 hours) (FIG. 1). On the other hand, REV 5901 reduced the late phase of inflammation but worsened the early phase (FIG. 2). OB-101 suppressed ocular inflammation (FIG. 3) as effectively as did prednisolone (FIG. 4) at both the early and late phases of inflammation. Based on OB-101 being as effective as prednisolone in the eye, OB-101 can be expected to be effective in fighting other types of inflammation in which prednisolone is effective, for example, arthritis, inflammatory bowel disease and pulmonary inflammation.

Example 3

Effects of OB-101 on Endotoxin-Induced Posterior Uveitis

A. Materials

OB-101 was synthesized with the method of Okawara et al. (see Example 1 above). Since OB-101 is not soluble in the aqueous medium, a suspension was prepared using a combined vehicle of Tween 80 (6%), PEG 400 (20%) and DMSO (20%), and the remainder distilled water.

Fluorescein labelled dextran with a molecular weight of 70,000 (FD 70) was obtained from Sigma and was prepared into a solution as described previously in the section on Fluorophotometric Methods in rabbit experiments with lens protein-induced inflammation (Example 2).

B. Methods

Sprague-Dawley rats weighing 250-350 grams were anesthetized with 35 mg/kg ketamine and 5 mg/kg xylazine intramuscularly. 10 μl of 10 ng endotoxin was injected intravitreally, and the animals were allowed to recover from the anesthesia. OB-101 at doses of 3 mg/kg and 10 mg/kg and prednisolone at a dose of 10 mg/kg were injected intraperitoneally at times 0, 4, and 10 hours after the endotoxin injection. The uveitis was measured with a Fluorotron (fluorophotometer) at 12 hours after the endotoxin injection. The procedure of Fluorotron measurement was the same as described previously in rabbit experiments with lens protein induced inflammation (Example 2). At the end of the experiments, the rats were euthanized with 100 mg/kg of pentobarbital sodium.

C. Results

All data were analyzed with Student's t-test for two values and analysis of variance for more than two values. Each value was expressed as mean ± standard error of the mean. A p value of 0.05 or less was considered significant.

Figure 5:
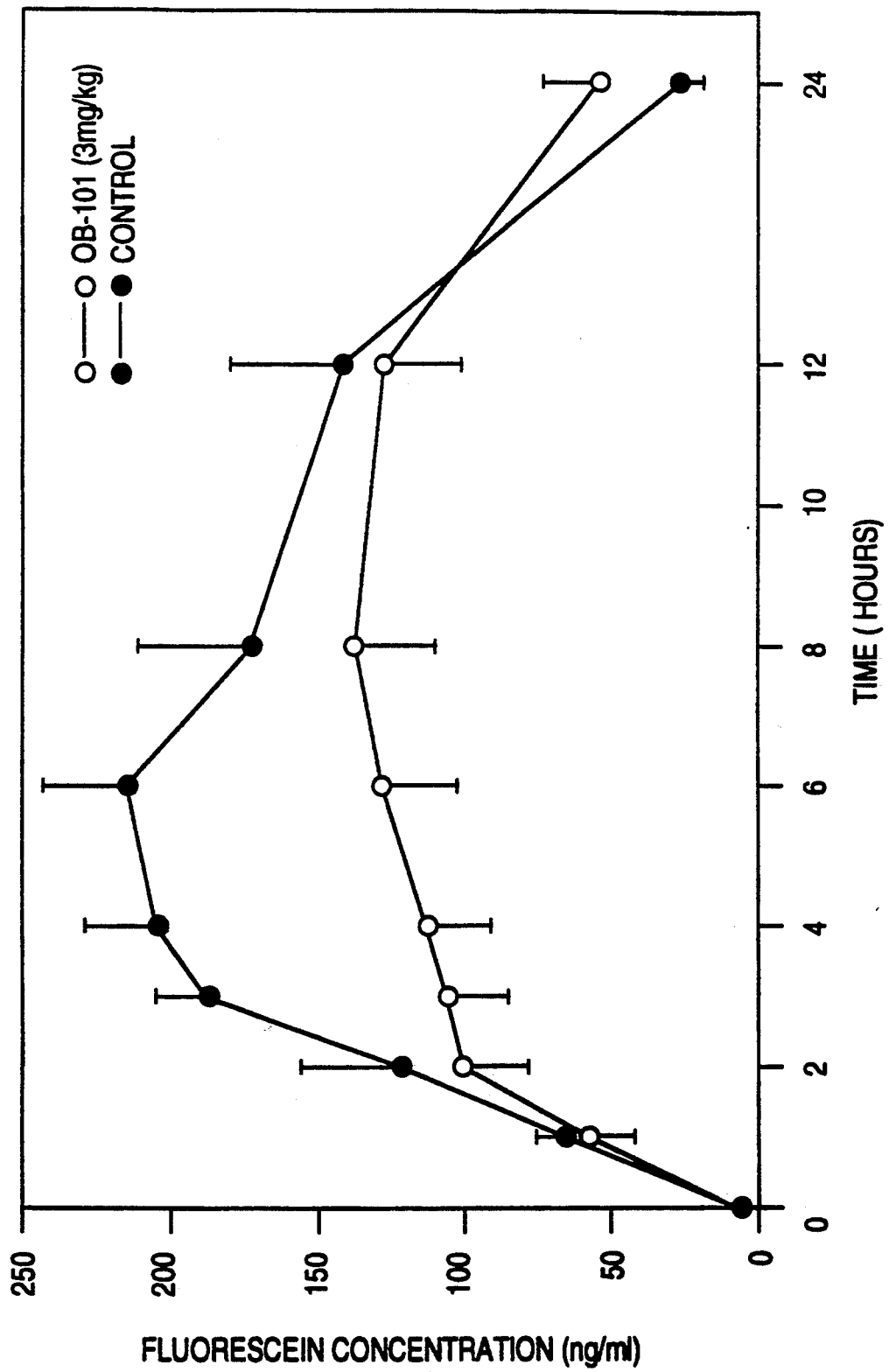
FIG. 5 shows a comparison of the effects of 3 mg/kg OB-101 delivered intraperitoneally on intravitreally injected endotoxin-induced uveitis to that of a control that received no drug. Each point is a mean of 9 values for fluorescein concentration in the posterior of the eye. The bars represent SEM and the asterisks indicate the significant difference from the corresponding control values at $p<0.05$.
Figure 6:
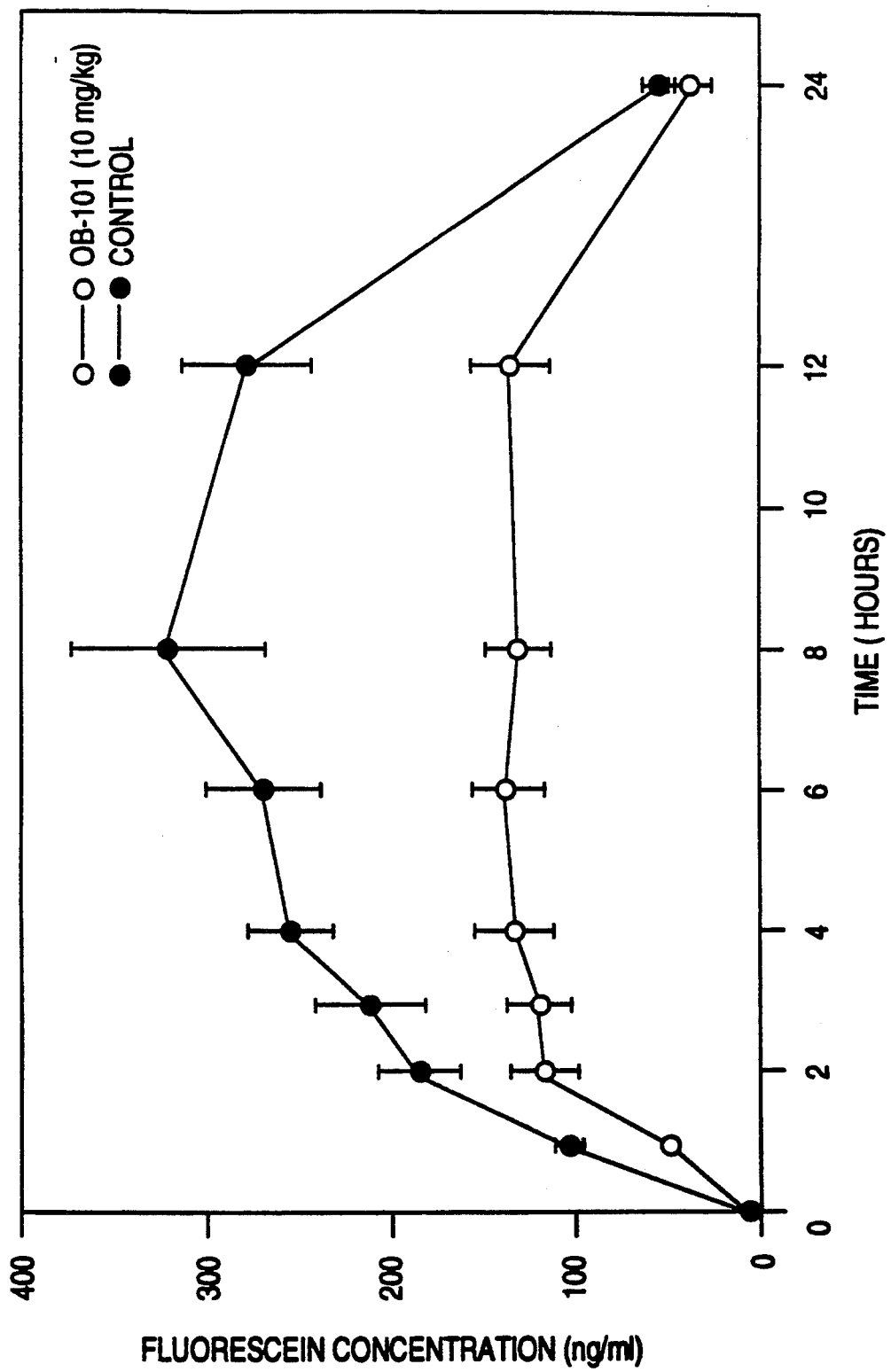
FIG. 6 shows a comparison of the effects of 10 mg/kg OB-101 delivered intraperitoneally on intravitreally injected endotoxin-induced uveitis to that of a control that received no drug. Each point is a mean of 9 values for fluorescein concentration in the posterior part of the eye. The bars represent SEM and the asterisks indicate the significant difference from the corresponding control values at $p<0.05$.

When fluorescein solution was injected intravenously into rats 12 hours after the endotoxin injection, the fluorescein reached peak in the eyes at 6-8 hours after the fluorescein injection. These peaks were suppressed 40% and 60%, respectively, by 3 mg/kg and 10 mg/kg of OB-101 as can be seen in FIGS. 5 and 6. In the case of 3 mg/kg OB-101, uveitis responses measured at 3, 4 and 5 hours after fluorescein were suppressed significantly at an average inhibition of 43% (FIG. 5). In the case of 10 mg/kg OB-101, all uveitis responses measured at 1, 2, 3, 4, 6, 8, and 12 hours after fluorescein injection were suppressed significantly (FIG. 6). During the experiments, no obvious side effects were noted as a result of the treatment of the animals with OB-101.

Figure 7:
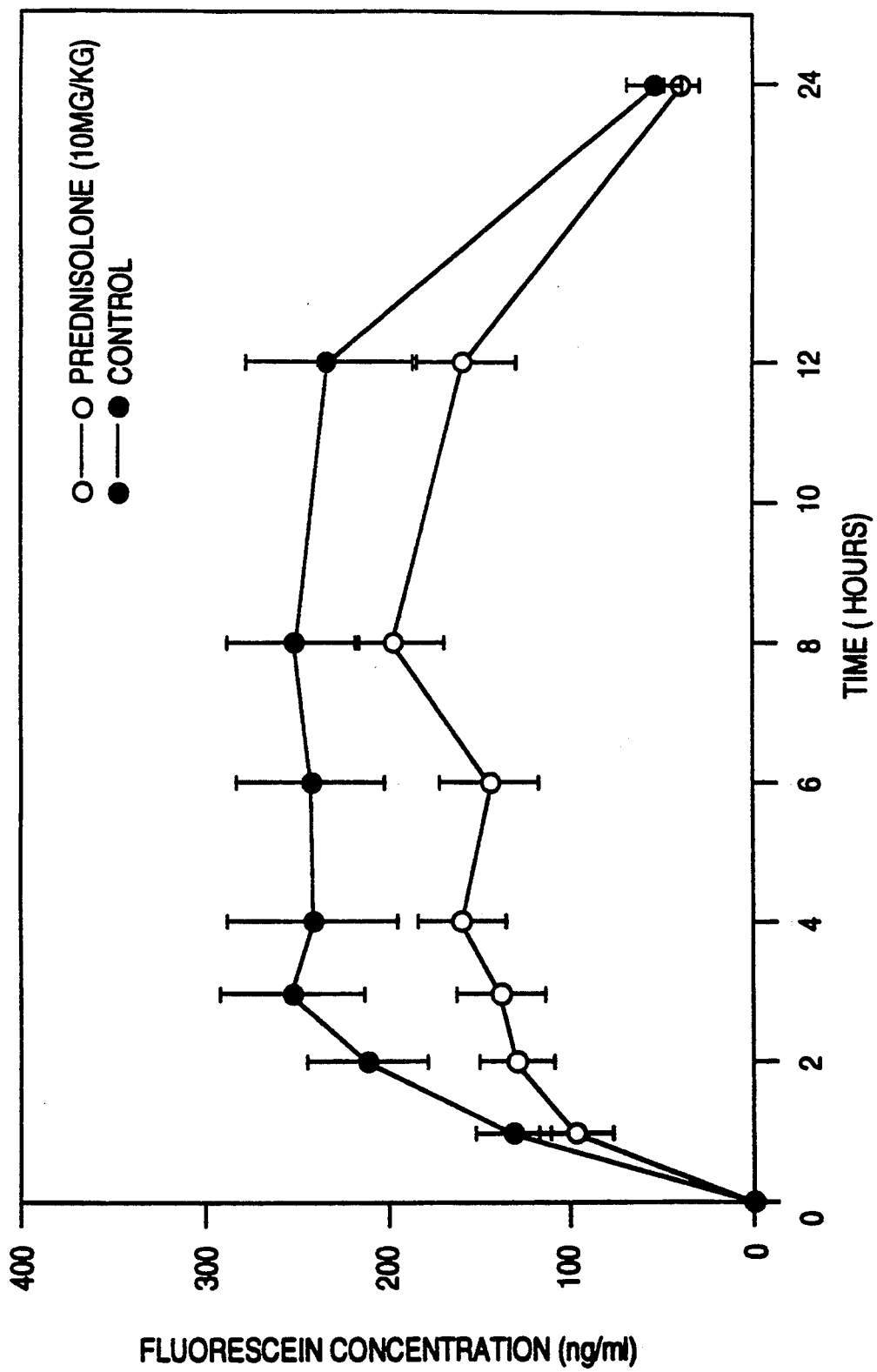
FIG. 7 shows a comparison of the effects of 10 mg/kg prednisolone delivered intraperitoneally on intravitreally injected endotoxin-induced uveitis to that of a control that received no drug. Each point is a mean of eight values for fluorescein concentration in the posterior part of the eye. The bars represent SEM and the asterisks indicate the significant difference from the corresponding control values at $p<0.05$.

FIG. 7 shows the inhibition of endotoxin induced uveitis by 10 mg/kg prednisolone. Uveitis responses measured at 2, 3, and 6 hours after fluorescein were suppressed significantly at an average inhibition of 42%. These results indicate that prednisolone is less potent than OB-101 to inhibit the posterior uveitis. This sideby-side test of systemic administration of prednisolone and OB-101 supports the Example 1 results indicating that OB-101 would have the same uses in fighting systemic inflammation as does prednisolone.

Example 4

Radioimmunoassay of PG's and LTB4

A. Materials

In order to determine the action mechanism of OB-101 to block ocular inflammation, radioimmunoassay (RIA) was used to determine the production of prostaglandins (PG's). The RIA was performed by using the kits purchased from Advanced Magnetics (Cambridge, Mass.). Kits were used to determine the concentration of prostaglandin ($PGE_2$ and $PGF_{2\alpha}$) and leukotriene ($LTB_4$) in the iris, ciliary body, and retina.

B. Methods

New Zealand albino rabbits of either sex weighing between 2.0 to 3.5 kg were used for this study. The rabbits were anesthetized by intramuscular injection of 25 mg/kg ketamine hydrochloride and 5 mg/kg xylazine. The anesthesia was maintained by injection of 12.25 mg/kg ketamine hydrochloride and 2.5 mg/kg xylazine every hour throughout the experiment. After the animals were deeply anesthetized, 50 μl of the drug was topically applied to one eye and the other eye received 50 μl of solvent. One hour after the application of the drugs, 25 μl of lens proteins was injected intracamerally with a 30 gauge needle; extreme care was taken to avoid contact with the iris. Animals were terminated by an overdose of sodium pentobarbital.

One group of animals was terminated at 2 and another at 4 hours after intracameral injection of the lens protein. After termination, the eyes were removed and dissected. The wet weight of iris, ciliary body, and retina was immediately obtained. The tissues were homogenized in 1 ml of normal saline acidified to pH between 3 and 4. Two ml of ethyl acetate was added to the homogenate and vortexed for 30 seconds. The homogenate was then centrifuged at 1000 × g for 20 minutes. The ethyl acetate layer of the homogenate was removed and evaporated under nitrogen. The tissue samples were then resuspended in buffer solution provided in the RIA kits. The prostaglandin RIA was performed in samples resuspended in 0.5 ml of buffer solution and the leukotriene RIA in samples resuspended in 0.3 ml buffer. The RIA was performed according to instructions provided in the kits. The RIA samples were centrifuged at 1000 × g for 20 minutes, after the addition of charcoal (provided in the RIA kit). The supernate was decanted and 5 ml of scintillation cocktail solution (Universal cocktail, ICN Biochemical, Irving, Calif.) was added. The samples were counted in a liquid scintillation counter (LS 5000 CE, Beckman, Fullerton, Calif.) for 10 minutes. The results were calculated per the instructions. The concentration of prostaglandin and leukotriene was expressed as pg/mg of tissue.

C. Results

All data were analyzed with Student's t-test for two values and analysis of variance for more than two values. Each value was expressed as mean ± standard error of the mean. A p value of 0.05 or less was considered significant.

The results of the RIA are shown in Tables 1 and 2. Indomethacin significantly reduced the concentration of $PGE_2$ and $PGF_{2\alpha}$ in the iris and ciliary body at 2 and 4 hours (Tables 1 and 2). REV 5901 only produced a significant decrease in $PGE_2$ levels in the ciliary body at 4 hours (Table 1). OB-101 produced a significant decrease of $PGE_2$ only in the iris but not in the ciliary body nor the retina. It did not show any decrease in $PGF_{2\alpha}$ in any tissue. Prednisolone did not produce any statistically significant change in the levels of $PGF_{2\alpha}$ or $PGE_2$ (Tables 1 and 2).

The prostaglandin level in the retina was lower than in the iris and ciliary body in all cases (Tables 1 and 2). This indicates that the inflammation induced by intracameral injection of lens protein does not affect the retina and that the topical application of drugs to the eye does not affect the retina either.

Attempts to determine the levels of leukotriene concentration in rabbit ocular tissue were abandoned after several attempts due to extremely low levels of leukotriene in the tissues: all measurements in iris, ciliary body, and retina were less than 6 pg/mg even after 8 hours after injection of the lens protein. Attempts were also made to measure the concentration of leukotriene in the aqueous humor after injection of lens

TABLE 1

EFFECTS OF ANTIINFLAMMATORY AGENTS ON $PGE_2$ PRODUCTION INDUCED BY LENS PROTEIN AT EARLY PHASE (2 HRS) AND LATE PHASE (4 HRS) OF INFLAMMATION

| DRUGS (1%) | N | CONTROL | | | TREATED | | |
|---|---|---|---|---|---|---|---|
| | | IRIS | CILIARY BODY | RETINA | IRIS | CILIARY BODY | RETINA |
| Early Phase | | | | | | | |
| Prednisolone | 4 | 95.9 ± 25.1 | 35.1 ± 1.0 | 10.0 ± 1.0 | 111.2 ± 4.1 | 59.1 ± 12.2 | 10.0 ± 1.7 |
| Indomethacin | 6 | 183.1 ± 42.0 | 93.5 ± 17.0 | 26.7 ± 19.0 | 22.5 ± 14.0* | 11.0 ± 2.0* | 10.3 ± 2.0 |
| REV 5901 | 8 | 183.8 ± 34.3 | 157.3 ± 35.5 | 39.0 ± 14.7 | 123.0 ± 46.0 | 120.0 ± 45.1 | 46.7 ± 18.0 |
| OB-101 | 4 | 257.5 ± 34.6 | 174.2 ± 32.7 | 18.1 ± 0.6 | 147.6 ± 25.9* | 134.4 ± 25.6 | 14.5 ± 1.6 |
| Late Phase | | | | | | | |
| PREDNISOLONE | 4 | 122.1 ± 48.3 | 61.3 ± 17.1 | 31.5 ± 12.2 | 61.5 ± 19.6 | 114.0 ± 45.5 | 22.9 ± 8.9 |
| INDOMETHACIN | 4 | 158.3 ± 22.0 | 129.1 ± 41.0 | 6.9 ± 2.6 | 27.5 ± 12.5* | 22.0 ± 8.5* | 33.3 ± 27.8 |
| REV 5901 | 6 | 185.5 ± 46.8 | 90.5 ± 22.8 | 13.3 ± 2.4 | 112.6 ± 43.3 | 51.6 ± 12.7* | 76.8 ± 18.1 |
| OB-101 | 4 | 207.5 ± 39.8 | 173.6 ± 31.2 | 16.1 ± 0.6 | 135.0 ± 26.8* | 156.0 ± 34.3 | 15.1 ± 1.2 |

*Indicates significantly different controls at $P < 0.05$.

TABLE 2

EFFECTS OF ANTIINFLAMMATORY AGENTS ON $PGF_{2\alpha}$ PRODUCTION INDUCED BY LENS PROTEINS AT EARLY PHASE (2 HRS) AND LATE PHASE (4 HRS) OF INFLAMMATION.

| | | | | | | | |
|---|---|---|---|---|---|---|---|
| Early Phase | | | | | | | |
| Prednisolone | 4 | 19.4 ± 4.8 | 7.1 ± 1.1 | 7.6 ± 1.1 | 20.3 ± 3.9 | 13.4 ± 4.8 | 15.2 ± 5.3 |
| Indomethacin | 6 | 50.2 ± 16.0 | 52.4 ± 16.3 | 12.6 ± 2.1 | 11.0 ± 8.0* | 13.0 ± 7.5* | 12.2 ± 3.7 |

TABLE 2-continued

EFFECTS OF ANTIINFLAMMATORY AGENTS ON $PGF_{2a}$ PRODUCTION INDUCED BY LENS PROTEINS AT EARLY PHASE (2 HRS) AND LATE PHASE (4 HRS) OF INFLAMMATION.

| | | | | | | | |
|---|---|---|---|---|---|---|---|
| REV 5901 | 6 | 26.6 ± 4.3 | 19.7 ± 4.4 | 16.5 ± 2.4 | 26.8 ± 6.2 | 19.5 ± 4.2 | 17.1 ± 4.7 |
| OB-101 | 4 | 88.8 ± 29.7 | 59.3 ± 21.0 | 10.4 ± 2.1 | 47.2 ± 7.1 | 46.1 ± 8.6 | 7.5 ± 0.5 |
| Late Phase | | | | | | | |
| PREDNISOLONE | 4 | 20.0 ± 9.7 | 11.8 ± 3.4 | 16.3 ± 5.0 | 13.8 ± 2.2 | 20.1 ± 7.8 | 12.8 ± 1.0 |
| INDOMETHACIN | 4 | 50.3 ± 20.4 | 56.1 ± 33.0 | 7.8 ± 1.4 | 3.1 ± 1.0* | 6.1 ± 1.7* | 17.2 ± 2.9 |
| REV 5901 | 8 | 39.8 ± 13.4 | 29.3 ± 7.4 | 17.6 ± 4.9 | 25.6 ± 5.3 | 22.3 ± 3.9 | 20.7 ± 6.7 |
| OB-101 | 4 | 45.1 ± 12.7 | 42.7 ± 7.2 | 11.7 ± 1.5 | 35.9 ± 5.7 | 38.1 ± 5.7 | 9.4 ± 2.0 |

*Indicates significantly different from controls at $P < 0.05$.

protein. The results were not significantly different from those obtained from ocular tissue.

Example 5

Effects on Accumulation of Leukocytes

A. Materials

In order to determine the mechanism of action of OB-101, the effects of the drug on the accumulation of leukocytes in the anterior chamber of the eye during inflammation was determined.

B. Methods

New Zealand albino rabbits of either sex weighing between 2.0 to 3.5 kg were used for this study. The rabbits were anesthetized by intramuscular injection of 25 mg/kg ketamine hydrochloride and 5 mg/kg xylazine. The anesthesia was maintained by injection of 12.25 mg/kg ketamine hydrochloride and 2.5 mg/kg xylazine every hour throughout the experiment. After the animals were deeply anesthetized, 50 μl of the drug was topically applied to one eye and the other eye received 50 μl of solvent. One hour after the application of the drugs, 25 μl of lens proteins was injected intracamerally with a 30 gauge needle; extreme care was taken to avoid contact with the iris. Animals were terminated by an overdose of sodium pentobarbital.

Animals were terminated at 4 hours after injection of lens protein. The aqueous humor was obtained from the eye by puncturing the cornea with a 23-gauge needle and a 3 cc syringe. After insertion of the needle into the anterior chamber, even mixing of the aqueous humor was ensured by suctioning and releasing several times with the syringe before drawing the sample. The aqueous humor was then placed in an improved Newbauer chamber and the leukocytes were counted.

C. Results

All data were analyzed with Student's t-test for two values and analysis of variance for more than two values. Each value was expressed as mean ± standard error of the mean. A p value of 0.05 or less was considered significant.

The results of the leukocyte counts are shown in Table 3. Prednisolone exhibited the greatest percent reduction in chemotaxis of leukocytes. OB-101 and REV 5901 also caused a significant reduction in leukocyte counts. Indomethacin, however, produced a significant increase in chemotaxis of leukocytes.

TABLE 3

EFFECTS OF ANTIINFLAMMATORY AGENTS ON LEUKOCYTE CHEMOTAXIS INDUCED BY LENS PROTEIN AT LATE PHASE OF INFLAMMATION

| DRUGS (1%) | N | CONTROL | TREATED | % CHANGE |
|---|---|---|---|---|
| PREDNISOLONE | 4 | 90.0 ± 20.4 | 10.0 ± 4.1* | −89 |
| INDOMETHACIN | 6 | 158.0 ± 41.0 | 298.0 ± 70.0* | +88 |
| REV 5901 | 6 | 395.0 ± 90.5 | 140.0 ± 30.5* | −65 |
| OB-101 | 4 | 612.5 ± 143.4 | 340.0 ± 34.9* | −45 |

*Indicates significantly different from control at $P < 0.05$

Modifications of the above described modes for carrying out the invention that are obvious to persons of skill in the art to which the invention pertains are intended to be within the scope of the following claims.

I claim:

1. A method for the treatment and prevention of inflammation in an animal subject which method comprises administering to said subject an inflammation-controlling effective amount of a pharmaceutical composition comprising a pharmaceutically acceptable vehicle in admixture with a compound having the formula

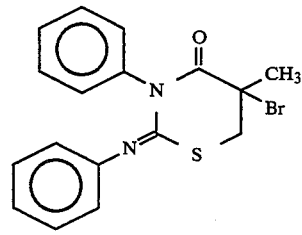

2. The method of claim 1 wherein the compound is administered orally.

3. The method of claim 1 wherein the compound is administered parenterally.

4. The method of claim 1 wherein the compound is administered topically.

5. The method of claim 1 wherein the inflammation is selected from the group consisting of arthritis, inflammatory bowel disease and pulmonary inflammation.

* * * * *